United States Patent [19]
Amelse

[11] Patent Number: 5,189,234
[45] Date of Patent: Feb. 23, 1993

[54] SELECTIVE DEHYDROGENATION PROCESSES AND CATALYSTS

[75] Inventor: Jeffrey A. Amelse, Batavia, Ill.

[73] Assignee: Amoco Corporation, Chicago, Ill.

[21] Appl. No.: 785,550

[22] Filed: Oct. 31, 1991

[51] Int. Cl.$^5$ .............................................. C07C 15/24
[52] U.S. Cl. ................................. 585/320; 585/400; 585/430; 585/440; 585/481
[58] Field of Search ............... 585/320, 400, 430, 440, 585/481

[56] References Cited

U.S. PATENT DOCUMENTS

| | | |
|---|---|---|
| 3,325,551 | 6/1967 | Suld . |
| 3,531,543 | 9/1970 | Clippinger et al. . |
| 3,775,496 | 11/1973 | Thompson . |
| 4,060,559 | 11/1977 | Goto et al. ........................ 502/237 |
| 4,268,707 | 5/1981 | Antos . |

FOREIGN PATENT DOCUMENTS

| | | |
|---|---|---|
| 0098622 | 1/1984 | European Pat. Off. . |
| 49-72240 | 7/1974 | Japan . |
| 1499297 | 1/1978 | United Kingdom . |

OTHER PUBLICATIONS

Imamura et al., Chemical Abstracts 31116q, vol. 82 (1975).

*Primary Examiner*—Patrick P. Garvin
*Assistant Examiner*—Brent M. Peebles
*Attorney, Agent, or Firm*—Thomas E. Nemo; Wallace L. Oliver; Frank J. Sroka

[57] ABSTRACT

A process for selectively dehydrogenating organic compounds, and particularly for dehydrogenating dimethyltetralins to dimethylnaphthalenes, by contacting the organic compound at an elevated temperature with a catalyst prepared by treating a composition comprising an alumina support material and platinum group metal with an excess amount of an alkaline solution of an alkali metal salt.

14 Claims, No Drawings

SELECTIVE DEHYDROGENATION PROCESSES AND CATALYSTS

FIELD OF INVENTION

This invention relates to processes and catalysts useful for the selective dehydrogenation of a dehydrogenatable organic compound. More particularly, this invention relates to processes and catalysts for the selective dehydrogenation of dimethyltetralins to dimethylnaphthalenes.

BACKGROUND OF THE INVENTION

The dehydrogenation of an organic compound to produce an unsaturated compound from a saturated organic compound, or to produce a more highly unsaturated organic compound from an already unsaturated compound, is a widely used industrial chemical process. For example, ethylbenzene or propylbenzene can be dehydrogenated to produce styrene and 2-methylstyrene, respectively, and the styrene monomers so-produced are useful for preparing polymeric compositions, e.g. polystyrenes. Linear alkanes can also be dehydrogenated to produce alkenes and these alkenes can be used to alkylate aromatic compounds. For example, benzene or toluene can be alkylated with high molecular weight linear olefins to produce alkylated intermediates useful for the preparation of surfactants and detergents. More recently, however, there has been interest in the preparation of dialkylnaphthalene compounds, for example, 2,6-dimethylnaphthalene, by the dehydrogenation of a dimethyltetralin. Dialkylnaphthalenes, and particularly 2,6-dimethylnaphthalene, are suitable feedstocks for oxidation to naphthalenedicarboxylic acid. 2,6-Naphthalenedicarboxylic acid, for example, is a monomer useful for preparing high performance polymers such as polyesters.

One suitable synthetic route for the preparation of 2,6-dimethylnaphthalene comprises reacting o-xylene with butadiene in the presence of a alkali metal catalyst to form 5-ortho-tolylpentene (5-OTP). The 5-OTP is cyclized to form 1,5-dimethyltetralin (1,5-DMT), which is then dehydrogenated to form 1,5-dimethylnaphthalene (1,5-DMN). The 1,5-dimethylnaphthalene can be isomerized to 2,6-dimethylnaphthalene (2,6-DMN). A process for preparing 5-OTP from o-xylene and butadiene is disclosed in, for example, U.S. Pat. No. 3,953,535 to Shima, et al. The cyclization process, which is depicted by the following equation, is disclosed in U.S. Pat. Nos. 5,030,781 and 5,034,561 to Sikkenga, et al.

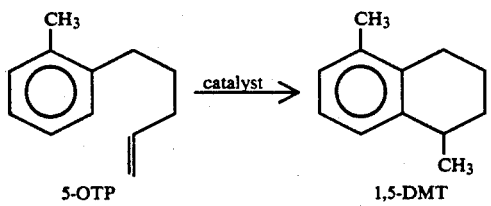

The dehydrogenation reaction where 1,5-DMT is converted to 1,5-DMN is typically conducted at elevated temperatures in the presence of a solid, heterogeneous dehydrogenation catalyst. The reaction is illustrated by the following equation:

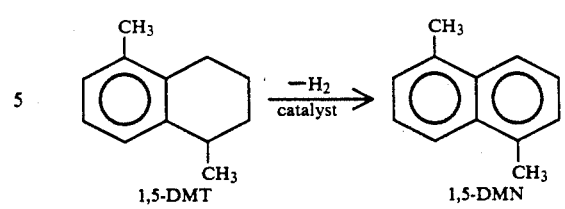

In order to make the overall process for converting o-xylene and butadiene to 2,6-dimethylnaphthalene acceptable for commercial-scale production, particularly because of the number of process steps, it is essential to have each reaction step be as selective as possible and to proceed in as high a yield as possible. Therefore, it is important to use a dehydrogenation catalyst that can catalyze the conversion of 1,5-DMT to 1,5-DMN in a highly selective and high yield manner.

A process for preparing dimethylnaphthalene from dimethyltetralins using heterogeneous catalyst is disclosed, for example, in U.S. Pat. No. 3,775,496 to Thompson, wherein a dimethyltetralin is dehydrogenated to a dimethylnaphthalene using a platinum on alumina catalyst. In the process disclosed therein, the dimethyltetralin is contacted with the solid dehydrogenation catalyst at a temperature in the range of about 300°–500° C. in the presence of hydrogen. It is also disclosed that it is preferable to use a platinum on non-acidic alumina catalyst. This patent also teaches that U.S. Pat. No. 3,325,551 to Suld discloses a method for preparing non-acidic dehydrogenation catalysts. In the method disclosed in the Suld U.S. Pat. No. 3,325,551 patent, a basic alkali metal salt, preferably lithium carbonate, is deposited on the catalyst. For example, an alumina support having platinum metal deposited thereon is saturated with an aqueous lithium carbonate solution after which the wet catalyst is heated to, for example, 150°–260° C., in order to remove the water. Methods for dehydrogenating dimethyltetralins to dimethylnaphthalenes are also disclosed in Sikkenga, et al. U.S. patent application Ser. No. 556,350, filed Jul. 20, 1990.

Methods for preparing non-acidic dehydrogenation catalysts are known in the art. For example, U.S. Pat. No. 4,268,707 to Antos teaches a method for preparing a non-acidic catalytic composition comprising a porous carrier material containing 0.01 to about 2 wt. % platinum group metal, about 0.05 to about 5 wt. % cobalt, about 0.1 to about 5 wt. % alkali metal or alkaline earth metal, and about 0.01 to about 5 wt. % lanthanide series metal. It is disclosed in the Antos patent that the alkali or alkaline earth metal component is added to neutralize any acidic material such as halogen which may have been present in the preparation of the catalyst so that the final catalyst is non-acidic. U.S. Pat. No. 3,531,543 to Clippinger et al. discloses catalyst compositions comprising a Group VIII noble metal component, tin and an inorganic refractory metal oxide carrier. The Clippinger et al. patent discloses that halogen can be removed from the composite prior to calcination by elutriation, ion-exchange, steaming, etc. British Patent Specification 1,499,297 discloses a method and a catalyst for dehydrogenating paraffin hydrocarbons. The catalysts disclosed therein comprise a carrier of active alumina having deposited thereon platinum in an amount of from 0.2 to 1.0% by weight, an alkali metal in an amount of from 0.2 to 2.0% by weight, and at least one of the three elements gallium, indium and thallium in a total amount of from 0.2 to 1.0% by weight, all percentages being with respect to the weight of the catalyst. This British Patent Specification also discloses that when a halogen is incorporated during the catalyst preparation, for example, by impregnating the carrier with chlorine-containing compounds of platinum, the impregnated, dried and calcined carrier should be subjected to a treatment to reduce the halogen content in the catalyst. It is taught that the impregnated, dried and calcined carrier may be treated with an aqueous solution of ammonia at a temperature of from 50° to 90° C. to reduce the halogen content in the catalyst to from 0.01 to 0.1% by weight.

The art, however, needs improved processes and catalysts that can be used for the selective dehydrogenation of organic compounds and particularly for the dehydrogenation of dimethyltetralins to dimethylnaphthalenes. The present invention provides such improved processes and catalysts.

SUMMARY OF INVENTION

Disclosed is a process for dehydrogenating dehydrogenatable organic compounds comprising contacting the organic compound at an elevated temperature with a catalyst formed by the steps comprising: contacting a composition comprising a platinum group metal component on an alumina support material with an alkaline solution of an alkali metal salt, the amount of solution being in excess of the amount absorbed by the composition; partitioning the composition from remaining solution to form a treated composition and a filtrate; and drying the treated composition to form the catalyst. This process can be used to selectively dehydrogenate organic compounds and, in particular, this process can be used for the dehydrogenation of dimethyltetralins to dimethylnaphthalenes.

This invention is also a method for preparing selective dehydrogenation catalysts and the catalysts prepared by such method.

DETAILED DESCRIPTION OF THE INVENTION

The catalysts that are used in the process of this invention for dehydrogenating organic compounds are the catalysts comprising an alumina support material, also called a carrier material, and a platinum group metal. The catalysts are prepared by treating a composition comprising an alumina support material and at least one platinum group metal with an excess amount of an aqueous alkaline solution of an alkali metal salt. This treatment provides for catalysts having enhanced selectivity for chemical transformations such as dehydrogenation reactions.

The alumina support material is any type of alumina. However, crystalline aluminas known as gamma-, eta- and theta-alumina are preferable. Gamma-alumina and eta-alumina are the most preferred. The alumina support can also be a mixture of one or more aluminas. Additionally, the alumina may contain minor proportions of other support materials such as for example, zirconia, magnesia and titania. Preferably, the alumina support material is highly-porous, adsorptive and has a high surface area such as in the range of about 25 to about 500 square meters per gram.

The platinum group metal component includes one or more of platinum, palladium, iridium, osmium, ruthenium and rhodium. The platinum group metal component or mixture of platinum group metals should be present in the catalyst in an amount in the range of about 0.05 wt % to about 5 wt %, and preferably about 0.25 wt % to about 1 wt %. Platinum and palladium are the preferred platinum group metals, and platinum is the most preferred platinum group metal. In addition to containing the platinum group metal, the catalyst can contain other metal components that are known in the art to promote the effectiveness of the platinum group metal in chemical reactions such as hydrogenation reactions and dehydrogenation reactions. For example, tin and rhenium, particularly when present in minor amounts relative to the platinum group metal component, are suitable promoter metals.

The platinum group metal component may be added to the alumina support material by any known manner that produces a relatively uniform distribution of the platinum metal component on the alumina support. The preferred method, however, is by impregnation of alumina pre-shaped, for example, as spheres, pills, cakes, powders or extrudates in any desired size. The impregnation involves contacting the alumina with a solution of a decomposable platinum group metal compound so as to impregnate the alumina in a relatively uniform manner. For example, the alumina support can be contacted with an aqueous solution of chloroplatinic acid, chloropalladic acid or chloroiridic acid. However, other water soluble compounds or complexes of the platinum group metals can also be used including, for example, ammonium chloroplatinate, bromoplatinic acid, platinum trichloride, platinum tetrachloride hydrate, dinitrodiamino platinum, sodium tetranitroplatinate (II), palladium chloride, palladium nitrate, palladium dioxide, diaminepalladium (II) hydroxide, tetraaminepalladium (II) chloride, hexamine rhodium chloride, rhodium carbonylchloride, rhodium trichloride hydrate, rhodium nitrate, sodium hexachlororhodate (III), sodium hexanitrorhodate (III), iridium tribromide, iridium dichloride, iridium tetrachloride, sodium hexanitroiridate (III), potassium chloroiridate, potassium rhodium oxalate, and the like. Ordinarily, the use of a platinum, iridium, rhodium, or palladium chloride compound is preferred for impregnating the alumina support. In addition, compounds such as nitric acid, hydrogen chloride, hydrogen bromide, aluminum chloride, and ammonium chloride are used to assist in the dispersion of the platinum metal. In order to avoid the loss of the valuable platinum group metal from the alumina, it is desirable to add the platinum metal to the alumina support material after the alumina has been pre-shaped and calcined. However, after the platinum group metal is added to the alumina support, the composition can be calcined at temperature in the range of about 800° F. to about 1200° F.

While the compositions treated with the aqueous solution of alkali metal salt may be prepared by any known procedure, and particularly those procedures described above, this treatment is especially useful for treating compositions that contain a halogen component that is residual from the procedure used to impregnate the alumina support material. The halide can be at least about 0.20 weight percent of the composition, and typically at least about 0.50 weight percent of the composition. The treatment of such a composition with an excess amount of an aqueous solution of an alkali metal salt removes a major portion of the residual halogen, for example chloride, that is believed to adversely affect the selectivity of the catalyst. Also, in addition to treating compositions made by the hereinabove-described procedures, this treatment with an excess amount of an aqueous solution of an alkali metal salt can also be used to increase the performance, i.e. selectivity, of commercially available catalyst compositions containing an alumina support and one or more platinum group metal components, and particularly those commercial catalysts containing chloride.

When preparing the catalysts used in the dehydrogenation process of this invention, the composition comprising an alumina support material and a platinum group metal component, as described above, is contacted with an excess amount of an aqueous alkaline solution of an alkali metal salt. By excess, it is meant that there is sufficient solution to saturate the composition and still have a portion of the solution remain unabsorbed, i.e. the amount of solution contacted with the composition is an amount in excess of that absorbed by the composition. Preferably, the amount of solution is at least about 1 part of solution by weight per part by weight of the composition, preferably at least about 2 parts and most preferably at least about 5 parts by weight of solution per part by weight of the composition. When the composition contains chloride or other halide, the excess solution solubilizes and removes halide from the composition.

The amount of solution used to contact the composition or the concentration of alkali metal salt in the solution preferably should be sufficient such that the solution partitioned from the composition after contact with the composition has a pH above about 7 and preferably a pH above about 8. When the composition comprising an alumina support material and platinum group metal also contains chloride, the amount of solution used to contact the composition should be an amount sufficient to reduce the chloride in the final treated composition to a level not greater than about 0.14 wt %, preferably not greater than about 0.12 wt %, as measured by X-ray fluorescence spectroscopy.

The alkali metal salt used to prepare the aqueous alkaline solution is any alkali metal salt that provides for an alkaline solution when dissolved in neutral pH water. The preferred alkali metal salts are the salts of lithium, sodium and potassium. Sodium salts are the most preferred alkali metal salts. The anionic portion of the salt can be any anion that provides for an alkaline solution when the salt is dissolved in neutral pH water; for example, an alkoxide or phenoxide. However, the preferred anionic components are bicarbonate, carbonate, oxide, and hydroxide, with carbonate and bicarbonate being most preferred. Due to availability and cost, sodium carbonate and sodium bicarbonate are the most preferred salts for preparing the alkaline solutions. Preferably, the alkaline solution used to contact the composition has a pH in excess of about 8, preferably in excess of about 10. Suitable solutions are prepared by dissolving about 1 to about 100, preferably 1 to about 50 parts, by weight, of the alkali salt in 1000 parts by weight of water. Preferably, the water used is distilled water or some other form of highly pure water. Pure water decreases as much as possible the contamination of the catalyst with extraneous metals or other impurities.

The procedure used to contact the solution with the composition comprising an alumina support material and a platinum group metal component is any suitable means for contacting an insoluble solid component with a liquid component. For example, the composition can be soaked in the solution, or the solution can be passed through a zone containing the composition, such as a fixed bed of the composition. The temperature at which the solution is contacted with the composition is suitably about 30° F. to about 90° F., however, higher or lower temperatures can also be used. The time during which the composition is in contact with the alkaline solution of the alkali metal salt is a time sufficient to provide for a selective dehydrogenation catalyst. This time is suitably about 1 minute to about 1 hour, although shorter or longer contact times can be used, depending on the amount of solution used and the concentration of the alkali metal salt in the solution.

After the treatment of the composition with a solution of an alkali metal salt, the composition can be dried and used as a catalyst for dehydrogenating organic compounds. However, before drying, the composition can be contacted with water, preferably distilled or purified water, to remove additional amounts of absorbed alkaline solution. The procedure used to contact the treated composition with water is suitably one or more of the procedures described above for contacting the untreated composition with the alkaline solution of the alkali metal salt. The amount of water used is suitably at least about 0.50 parts by weight of water per part by weight of the composition and perferably about 1 to about 100 parts by weight of water per part by weight of the composition, although lesser or greater amounts of water can be used. This treatment with water is referred to as a wash step because, as discussed above, it removes or "washes" additional alkaline solution from the composition.

If such a wash step is used, it is not necessary to use an amount of the alkaline solution of the alkali metal compound in excess of that absorbed by the composition because the wash step will effectively remove remaining alkaline solution absorbed along with any undesirable components dissolved in the alkaline solution. However, it is nevertheless preferable to use an amount of the alkaline solution in excess of the amount that can be absorbed by the composition even when a wash step is used, particularly when the composition contains chloride or some other halide.

After the wash step, if used, the composition can be dried and used as a catalyst. However, it is advantageous to contact the composition a second time with a solution of an alkali metal salt. The alkali salt can be any soluble salt providing it does not contain a halogen anion or other halogen component. For example, sodium, potassium or lithium nitrates, phosphates, sulfates, etc. can be used. However, it is most preferable to use a carbonate or bicarbonate of an alkali metal. Solutions of these basic salts remove, for example, additional halide if present. Sodium carbonate and bicarbonate are the most preferred basic salts for this second treatment.

It is advantageous for the final catalyst to contain some alkali metal. The amount of alkali metal is suitably more than about 0.10 weight percent, preferably about 0.10 to about 2.0 weight percent, and most preferably about 0.5 to about 1.0 weight percent, based on the weight of the catalyst. The alkali metal is preferably sodium or potassium, and most preferably sodium.

Prior to use as a catalyst, the treated composition is typically dried to remove any remaining water, and can be heated up to about 1200° F. to calcine the composition. Any suitable means for drying the composition can be used. For example, the composition can be heated in a stream of air or inert gas. The composition can also be dried in the reactor in which it will be used. For example, if the composition will be used as a catalyst in a gasphase reactor, the wet composition can be loaded into the reactor and dried during the first few hours of operation. If the composition is to be used as a catalyst in a liquid phase, batch-type reactor, it can be heated to above about 200° F. to remove the water in the presence of the liquid reactant. The procedure used for drying the catalyst is not critical. Before using the composition as a catalyst, however, it is preferably to first dry and then calcine the composition at a temperature in the range of about 800° F. to about 1200° F. for about 1 hour to about 12 hours to form the final catalyst.

The catalysts prepared as described above are particularly useful for dehydrogenating dehydrogenatable organic compounds. "Dehydrogenatable," as used herein, means that the organic compound contains at least one pair of adjacent carbon atoms having at least one hydrogen atom attached to each adjacent carbon atom. Preferably, the organic compound is a hydrocarbon, and more preferably a hydrocarbon having 2 to about 50 carbon atoms. The hydrocarbon can be cyclic, linear or branched. For example, linear alkanes containing about 2 to about 30 carbon atoms can be dehydrogenated to the corresponding linear olefin. The hydrocarbon can also be an alkyl aromatic such as, for example, ethylbenzene. Specific examples of dehydrogenatable hydrocarbons are ethane, propane, n-butane, isobutane, n-pentane, isopentane, n-hexane, branched hexanes (i.e. 2-methylpenatane), cyclopentane, cyclohexane, cyclohexene, methylcyclopentane, methylcyclohexane, 1,2-, 1,3- and 1,4-dimethylcyclohexane, decalin, tetralin, the methyl decalins, the methyl tetralins, the dimethyldecalins and the dimethyltetralins.

In a preferred embodiment, the dehydrogenatable organic compound is a dimethyldecalin (i.e. dimethyl decahydronaphthalene) or a dimethyltetralin (i.e. dimethyl-1,2,3,4-tetrahydronaphthalene). The dimethyldecalins include 1,2-, 1,3-, 1,4-, 1,5-, 1,7-, 1,8-,2,3-, 2,6- and 2,7-dimethyldecalins. The dimethyltetralins include, 1,2-, 1,3-, 1,4-, 1,5-, 1,6-, 1,7-, 1,8-, 2,3-, 2,5-, 2,6-, 2,7-, 2,8-, 5,6-, 5,7-, 5,8- and 6,7-dimethyltetralin. The dimethyldecalins and dimethyltetralins are suitably dehydrogenated to the corresponding dimethyl napthalenes in the process of this invention. The equation below illustrates these dehydrogenation reactions wherein the methyl groups are in a 2,6-relation to each other:

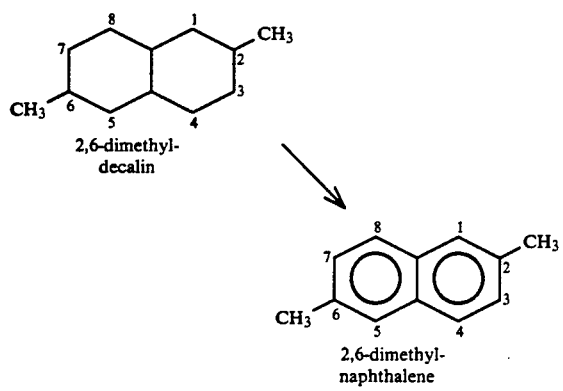

2,6-dimethyl-
decalin 2,6-dimethyl-
naphthalene

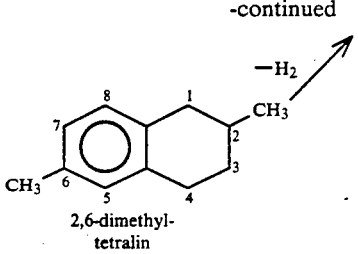

2,6-dimethyl-
tetralin

The dehydrogenation reactions using the catalysts prepared according to the method disclosed herein are suitably conducted in a liquid phase reaction or, preferably, in a gas phase reaction. In a liquid phase reaction, the dehydrogenatable feed material is contacted with the catalyst while the feed material is in the liquid phase. The temperature for the dehydrogenation is such that the dehydrogenation reaction proceeds at a suitable rate and, although the temperature required for the dehydrogenation will depend on the nature of the compound being dehydrogenated, suitable temperatures are in the range of about 200° F. to about 1000° F. The pressure used is a pressure sufficient to maintain a major portion of the reactants and products in the liquid phase. The reactor used to conduct the liquid phase dehydrogenation reaction is any suitable reactor including a fixed bed reactor, a stirred tank reactor, etc. For the dehydrogenation of the dimethyltetralins and dimethyldecalins in the liquid phase using the catalysts prepared according to the method of this invention, the reaction temperatures are suitably in the range of about 300° F. to about 750° F., preferably about 350° F. to about 650° F.

In the preferred dehydrogenation process of this invention, dehydrogenatable organic compounds are dehydrogenated in the vapor or gas phase. In this type of dehydrogenation reaction the dehydrogenatable feed is passed over the catalyst while the feed is in the vapor or gaseous phase. As discussed hereinabove for the liquid phase dehydrogenation reactions, the temperature used to dehydrogenate the dehydrogenatable hydrocarbon is any suitable temperature that provides for the formation of the dehydrogenated compound at a suitable rate. However, suitable temperatures are in the range of about 200° F. to about 1000° F. The pressure for the gas phase dehydrogenation reaction using the catalysts prepared by the method disclosed herein should be a pressure low enough to maintain the specific feed material in the gaseous phase. Typical weight hourly space velocities for the gas phase dehydrogenation reactions (i.e. weight of feed per weight of catalyst per hour) are in the range of about 0.10 to about 20 hr.$^{-1}$.

It should be understood that the preferred reaction conditions depend upon the compound being dehydrogenated. Dehydrogenation reactions are generally endothermic reactions, and high equilibrium conversion is favored by high temperature, low pressure, and low hydrogen-to-hydrocarbon mole ratio. On the other hand, catalyst deactivation is generally minimized by operating at low temperature, high pressure, and high hydrogen-to-hydrocarbon mole ratio. Thus, the choice of suitable reaction conditions requires a balance between the thermodynamic restrictions and the desire to achieve a reasonable catalyst life cycle.

For the gas phase dehydrogenation of the dimethyltetralins according to the process of this invention, the temperature for the dehydrogenation is suitably in the range of about 500° F. to about 1000° F., and preferably about 600° F. to about 900° F. The pressure is suitably in the range of about 0 psig to about 300 psig, preferably about 25 psig to about 200 psig. The weight hourly space velocity is suitably about 0.1 hr.$^{-1}$ to about 20 hr.$^{-1}$, preferably about 1.0 hr.$^{-1}$ to about 5.0 hr.$^{-1}$. The dimethyltetralin can be added to the gas phase reaction in pure form or in the presence of one or more other materials such as a diluent. Additionally, it is preferable to include a quantity of hydrogen along with the dimethyltetralin during the gas phase dehydrogenation to minimize catalyst deactiviation. The amount of hydrogen, on a mole basis, is suitably about 0.1 to about 25 moles of hydrogen per mole of dimethyltetralin, and preferably about 1 to about 10 moles of hydrogen per mole of dimethyltetralin. The preferred dimethyltetralins dehydrogenated by the catalysts prepared according to the method of this invention are 1,5-, 2,5-, 1,6- and 2,6-dimethyltetralin. The dimethylnaphthalenes prepared by the dehydrogenation of 1,5-, 2,5- and 1,6-dimethyltetralin, i.e. 1,5- and 1,6-dimethylnaphthalene, are suitable dimethylnaphthalenes for preparing 2,6-dimethylnaphthalene.

The reactor used for conducting the gas phase dehydrogenation reaction is typically a tubular reactor charged with the solid catalyst and equipped with a means to maintain a predetermined reaction temperature and pressure. However, any suitable reactor configuration, including a multi-tubular reactor, can be used. The dehydrogenation of the dimethyltetralins, and particularly 1,5-, 1,6-, 2,5- and 2,6-dimethyltetralin, is an endothermic reaction. Therefore, if a tubular adiabatic reactor is used with a fixed catalyst bed, the product mixture exiting the reactor is cooler than the reaction feed mixture entering the reactor, and the reaction temperature profile across the catalyst bed varies from an initial high temperature to a low temperature at the exit end. The conversion that is achieved in an adiabatic reactor can be limited thermodynamically to a value lower than the desired conversion due to the low exit temperature. If the conversion of the dimethyltetralin feed material is insufficient using one reactor, additional tubular reactors can be arranged in series to conduct the dehydrogenation. In this configuration, the reaction mixture can be heated to a higher temperature before it is introduced into the next adiabatic reactor. It is most desirable to provide enough catalyst in each of the beds such that at the preselected conditions, the conversion in each reactor exceeds about 80% and preferably about 90% of the equilibrium conversion at the conditions present at the exit end of the reactor bed.

During the dehydrogenation of the preferred dimethyltetralins using the catalysts prepared by the method disclosed herein, some isomerization of the methyl groups about the naphthalene ring structure can occur. Catalysts produced by the herein disclosed method provide for less isomerization than the corresponding untreated catalysts. Additionally, and perhaps more significantly, a portion of the dimethyltetralin is "cracked", i.e. reduced to lower molecular weight or converted to saturated ring-opened components during the dehydrogenation reaction. However, the catalysts prepared by the disclosed method provide for substantially less cracking compared to the untreated catalysts making them superior catalysts for the dehydrogenation of a dimethyltetralin and particularly 1,5-, 1,6-, 2,5-, and 2,6-dimethyltetralin.

When the composition treated according to the method of this invention contains chloride, the result is a marked decrease in the chloride level. For example, a composition initially containing about 0.80 wt % chloride contained, after treatment with an excess amount of an alkaline solution of an alkali metal salt according to the method disclosed herein, less than about 0.12 wt % chloride. These low-chloride catalysts are particularly effective catalysts for the dehydrogenation of a dimethyltetralin to the corresponding dimethylnaphthalene. Therefore, this invention is also the dehydrogenation of dimethyltetralin, particularly 1,5-dimethyltetralin, to the corresponding dimethylnaphthalene, using a catalyst comprising an alumina support material, about 0.05 to about 5.0 weight percent of at least one platinum group metal component, and no more than about 0.14, and preferably about 0.0 to about 0.10 weight percent chloride. It is also advantageous for the catalyst to contain some alkali metal, preferably, more than about 0.10 weight percent alkali metal, more preferably about 0.10 to about 2.0 weight percent alkali metal. Most preferably, the dehydrogenation catalyst for the dehydrogenation of dimethyltetralin to dimethylnaphthalenes comprises an alumina support material, most preferably gamma alumina, having a surface area of about 50 square meters per gram to about 500 square meters per gram, platinum in an amount of about 0.2 to about 1 weight percent, and no more than about 0.12 weight percent chloride, preferably no more than about 0.10 weight percent chloride, and a sodium content of about 0.5 weight percent to about 1.0 weight percent, wherein all weight percents are with respect to total weight of the catalyst.

The following examples are provided to illustrate embodiments of the present invention, it being understood that they do not limit the scope thereof.

EXAMPLES

All of the Examples that follow were performed using a platinum catalyst composition in the form of 1/16 inch extrudates. The initial, untreated catalyst composition contained about 0.60 weight percent platinum and about 0.79 weight percent chloride. The untreated catalyst composition had a BET surface area of 189 square meters per gram, and a pore volume of about 0.42 cubic centimeters per gram, as measured by nitrogen adsorption. The support material was primarily gamma alumina derived from American Cyanamid PHF alumina. This catalyst is hereinafter referred to as the "Untreated Catalyst". The catalysts treated according to the methods disclosed herein are hereinafter referred to as "Treated Catalysts."

The procedure used for preparing the treated catalyst designated as "A4" in the Examples follows. This general procedure was used for all of the catalysts tested except that different alkali salts, quantities of alkaline solution and quantities of wash solution, as noted in the Examples and corresponding tables, were used.

To prepare treated catalyst A4, 10.0 grams of anhydrous sodium carbonate was dissolved in 500.0 grams of distilled water. This solution was added to 100.0 grams of the untreated platinum on alumina catalyst composition described above and the mixture was gently stirred for approximately 0.5 hour at room temperature. The extrudates were separated from the supernatant solution by filtration and 450.8 grams of filtrate were recovered. The filtrate was titrated to determine its chloride content using the Mohr method. For this titration approximately 0.1N silver nitrate, standardized against sodium chloride, was used with potassium chromate as an indicator. Prior to the titration, the filtrate was neutralized to a pH of about 7 using 10% nitric acid.

After treatment with the alkaline sodium carbonate solution, the catalyst extrudates were washed by adding 500.0 grams of distilled water to the wet catalyst and the mixture was gently stirred for approximately 0.5 hour at room temperature. The catalyst was separated from the excess solution by filtration and the filtrate was titrated for chloride content.

The wet catalyst was then treated with a solution containing 5.0 grams of anhydrous sodium carbonate dissolved in 250 grams of distilled water by adding the solution to the wet catalyst and gently stirring the mixture for about 0.5 hour. The catalyst was separated from the excess solution by filtration and the filtrate was titrated for chloride content.

The catalyst was dried at 329° F. for about 4 hours, heated to 950° F. over a four-hour period, and then maintained at 950° F. for four hours.

Based on the data from the titrations, a total of 0.685 gram of the 0.790 gram of chloride in the original untreated catalyst composition was removed. Approximately 0.613 gram of chloride was removed during the first treatment with alkaline solution, approximately 0.068 gram was removed during the water treatment and approximately 0.004 gram during the final treatment with the alkaline solution. Based on the chloride measured by titration, the final treated catalyst should have contained 0.105 wt % chloride. Analysis by x-ray fluorescence spectroscopy indicated that the final treated catalyst contained 0.11 wt % chloride and 0.63 wt % platinum. Thus, the chloride titration analysis and the analysis by X-ray fluorescence spectroscopy were consistent with each other. Also, the results of the platinum analysis indicated platinum was not lost during the washings and heat treatment. Analysis by atomic absorption spectroscopy indicated that the final treated catalyst contained 0.82 wt % sodium.

The treated catalysts were tested for their ability to dehydrogenate 1,5-dimethyltetralin (1,5-DMT) to 1,5-dimethylnaphthalene (1,5-DMN) in a vapor phase reaction. The reactor used for this testing was a 0.5 inch O.D. stainless steel reactor tube positioned in a tube furnace having three heating zones, each zone 4 inches long. Thermocouples located in a ⅛ inch stainless steel tube centered in the reactor tube were used to measure and regulate the temperature of the catalyst bed. Three thermocouples were used. They were positioned near the top, middle and bottom of the catalyst bed, which was located from about ¼ inch below the top of the middle zone to about ¼ inch above the bottom of the middle zone. The three thermocouples were used to control the top, middle and bottom furnace zones, respectively. Thus, an essentially uniform temperature profile could be maintained across the catalyst bed. All catalysts tested were crushed and screened to 25-45 mesh. LaRoche T-1061 alpha alumina was placed above and below the catalyst bed, and was also used as a catalyst diluent when necessary to insure that the catalyst bed covered most of the middle zone, as noted above.

Reaction temperatures, as noted in the following tables, were 600°, 800° and 825° F. The temperature was uniform across the length of the catalyst bed. Reactor pressure was typically 150 psig, and the space velocity (Weight Hourly Space Velocity—WHSV) was typically 2. Hydrogen was added with the 1,5-DMT in a mole ratio of approximately 10:1, respectively. The WHSV refers to the weight of the 1,5-DMT feed added.

In the following examples and tables, "DMT" means dimethyltetralin, "DMN" means dimethylnaphthalene, "MN" means methylnaphthalene, "TMN" means trimethylnaphthalenes, "Lights" refers to a mixture of components, including tolypentanes, having boiling points lower than the DMT's and DMN's.

Analyses of the organic compounds were conducted using capillary gas chromography. The gas chromatograph was equipped with a flame ionization detector. Atomic Absorption (AA) was used to measure the alkali metal concentrations in the catalysts, and x-ray fluorescence spectroscopy (XRF) was used to measure the levels of chlorine and platinum in the catalysts.

In the following examples, percent conversion (conv.) refers to the weight percent of the 1,5-DMT in the feed converted to other products, and percent selectivity (Sel. or Select.) for a given product is the weight of the product formed divided by the weight of the 1,5-DMT converted multiplied by 100.

EXAMPLE I

Table 1 provides detailed information for six treatment procedures and an analysis of the resulting treated catalysts. Under the entry "First Treatment" is provided the composition of the first alkaline solution contacted with the untreated catalyst. Also provided is the number of grams of this solution used per gram of untreated catalyst. Under the entry "First Wash" is provided the grams of distilled water used per gram of catalyst to wash the catalyst. Under the entry "Second Treatment," if applicable, is reported the composition and amount of the alkaline solution used to treat the catalyst a second time.

This data demonstrates that contacting an untreated catalyst composition containing 0.60 weight percent platinum and 0.79 weight percent chloride with an excess amount of a solution of sodium carbonate ($Na_2CO_3$), sodium bicarbonate ($NaHCO_3$), lithium carbonate ($Li_2CO_3$) or potassium carbonate ($K_2CO_3$) substantially reduces the level of chloride in the composition. The platinum levels are, in general, not significantly reduced. These data show that most of the chloride is removed by the first treatment with the alkaline solution. As shown by the entries for catalyst E, distilled water was ineffective at removing chloride.

EXAMPLE II

Table II provides data for the dehydrogenation of 1,5-dimethyltetralin to 1,5-dimethylnaphthalene using treated catalysts A, B, D and F from Example I. The performance of these treated catalysts is compared to the performance of untreated catalyst. These data demonstrate that treated catalysts A, B, D and F are considerably more selective catalysts for dehydrogenating 1,5-dimethyltetralin to 1,5-dimethylnaphthalene. The selectivity for this conversion using the treated catalysts ranged from about 87.6 percent for the catalyst treated with lithium carbonate to about 95.1 percent for the catalyst treated with sodium carbonate. The selectivity for the untreated catalyst was only about 44.0 percent.

TABLE I

| | Catalyst | | | | | |
|---|---|---|---|---|---|---|
| | A | B | C | D | E | F |
| Salt Used | Na$_2$CO$_3$ | Na$_2$CO$_3$ | NaHCO$_3$ | Li$_2$CO$_3$ | (None) | K$_2$CO$_3$ |
| First Treatment: | | | | | | |
| gm salt/1000 gm water | 40.0 | 15.0 | 20.0 | 5.0 | 0.0 | 52.3 |
| gm soln./gm cat. | 5.0 | 2.5 | 2.5 | 5.0 | 2.5 | 2.5 |
| First Wash: gm/gm cat. | 10.0 | 5.0 | 5.0 | 10.0 | — | 5.0 |
| Second Treatment: | | | | | | |
| gm salt/1000 gm water | 20.0 | — | — | — | — | 52.5 |
| gm soln./gm cat. | 2.5 | — | — | — | — | 2.5 |
| Second Wash gm/gm cat. | — | — | — | — | — | 5.0 |
| % Soln. Removed by Decanting First Treatment | 83.4 | 74.4 | 73.2 | 88.3 | 70.0 | 73.1 |
| % Chloride Removed, Wt. (measured by titration) | | | | | | |
| First Treatment | 86.8 | 69.1 | 69.9 | 76.9 | 2.4 | 71.0 |
| First Wash | 8.4 | 19.1 | 18.0 | 14.0 | — | 17.4 |
| Second Treatment | 0.7 | — | — | — | — | 1.2 |
| Second Wash | — | — | — | — | — | 0.4 |
| Total | 95.9 | 88.2 | 87.9 | 90.9 | 2.4 | 90.0 |
| Analyses of Treated Cat., Wt. % | | | | | | |
| Pt, XRF | 0.57 | 0.58 | 0.58 | 0.60 | — | 0.53 |
| Cl, XRF | 0.12 | 0.11 | 0.11 | 0.10 | — | 0.10 |
| Na, AA | 1.10 | 0.32 | 0.24 | — | — | — |
| K, AA | — | — | — | — | — | 1.35 |
| Li, AA | — | — | — | 0.08 | — | — |

TABLE II

| | Catalyst | | | | |
|---|---|---|---|---|---|
| | A | B | D | F | Untreated |
| Salt Used | Na$_2$CO$_3$ | Na$_2$CO$_3$ | Li$_2$CO$_3$ | K$_2$CO$_3$ | — |
| Components, Wt. % | Feed | | Products$^a$ | | |
| Lights | 10.98 | 11.25 | 11.08 | 12.23 | 11.50 | 10.64 |
| 1,5-DMT | 76.23 | 1.33 | 1.11 | 1.34 | 1.95 | 0.76 |
| 1,6 + 2,5-DMT | 7.85 | 0.15 | 0.13 | 0.19 | 0.22 | 0.61 |
| Other DMT | 2.60 | 0.24 | 0.21 | 0.22 | 0.25 | 0.41 |
| 1-MN | 0.0 | 2.54 | 2.63 | 5.50 | 3.17 | 2.75 |
| 2-MN | 0.0 | 0.17 | 0.19 | 0.42 | 0.21 | 1.16 |
| 1,5-DMN | 1.63 | 72.86 | 72.95 | 67.24 | 71.25 | 34.84 |
| 1,6-DMN | 0.46 | 7.88 | 7.98 | 8.77 | 7.76 | 32.82 |
| 2,6-DMN | 0.05 | 0.25 | 0.27 | 0.34 | 0.26 | 8.56 |
| 1,7-DMN | 0.05 | 1.54 | 1.56 | 1.65 | 1.52 | 3.02 |
| 1,8-DMN | 0.0 | 0.21 | 0.19 | 0.04 | 0.17 | 0.01 |
| 2,7-DMN | 0.0 | 0.10 | 0.10 | 0.12 | 0.11 | 1.06 |
| Other DMN | 0.0 | 0.05 | 0.07 | 0.10 | 0.07 | 0.09 |
| TMN & Heavies | 0.18 | 1.45 | 1.54 | 1.84 | 1.56 | 1.26 |
| % Select. 1,5-DMT to 1,5-DMN | | 95.1 | 95.0 | 87.6 | 93.7 | 44.0 |

$^a$Conditions: 825° F., ~150 PSIG, H$_2$/Hydrocarbon mole ratio = 10, feed LWHSV = 2

EXAMPLE III

Table III provides data for a series of catalysts A1–A6 prepared by contacting untreated platinum on alumina catalyst with solutions of sodium carbonate. The total procedure comprises a first treatment, followed by a wash, and then a second treatment. The concentration of sodium carbonate in the solution used for the first treatment was varied as shown. The wash and the second treatment with an alkaline solution was, however, the same for treated catalysts designated A1 through A6. These data demonstrate that sodium carbonate is effective for reducing the chloride levels of the untreated catalyst. These data also demonstrate that the amount of chloride removed appears to be dependent on the concentration of sodium carbonate in the solution used for the first treatment. This effect is evident by a comparison of the analytical data for catalyst designated A5 and A6 compared to catalysts A1–A4.

EXAMPLE IV

Table IV provides data for the conversion of 1,5-dimethyltetralin to 1,5-dimethylnaphthalene using catalyst A1–A6 in Example III at dehydrogenation reaction temperatures of 600° F. and 800° F.

These data demonstrate that at 800° F. the conversion and selectivity are excellent for the treated catalysts. However, it is apparent that catalysts A1, A2 and A4, the catalysts with lower chloride content, are superior to catalysts A5 and A6 which have the higher chloride content. Catalyst A5 and A6 provide for lower selectivity and produce more "lights" compared to catalyst A1, A2 and A4. Catalysts A5 and A6 were prepared using less concentrated solutions of sodium carbonate in the first treatment.

For the dehydrogenation reactions of 1,5-dimethyltetralin to 1,5-dimethylnaphthalene conducted at 600° F., the conversion was lower compared to the reaction conducted at 800° F., due to thermodynamic limitations at the lower temperature. At the lower temperatures that can occur at the end of the first in a series of adiabatic reactor beds, the cracking reaction competes with the dehydrogenation reaction which leads to the formation of "lights". These data, however, also demonstrate that the catalysts containing more chloride are less selective catalysts.

EXAMPLE V

Table V provides data for a series of catalysts A7–A12 prepared by contacting the untreated platinum on alumina catalyst with solutions of sodium carbonate. As with the procedure used to prepare the treated catalysts in Example III, the procedure used incorporated a first treatment, a wash, followed by a second treatment. The concentration of sodium carbonate in the solution used for the first treatment was the same for preparation of treated catalysts A7–A12, and except for catalyst A8, the same amount of water was used to wash the catalysts. However, the concentration of sodium carbonate in the solution used for the second treatment was varied for catalysts A7–A12.

These data show that the amount of chloride removed is, except for catalyst A7 where no base was used for the second treatment, about the same when the same amount and concentration of sodium carbonate solution is used to treat the catalyst during the first treatment. However, the sodium content of the treated catalyst increased with the sodium carbonate concentration of the second treatment.

TABLE III

|  | Catalyst | | | | | |
|---|---|---|---|---|---|---|
|  | A1 | A2 | A3 | A4 | A5 | A6 |
| Salt Used | $Na_2CO_3$ | $Na_2CO_3$ | $Na_2CO_3$ | $Na_2CO_3$ | $Na_2CO_3$ | $Na_2CO_3$ |
| First Treatment: | | | | | | |
| gm salt/1000 gm water | 10.0 | 10.0 | 5.0 | 20.0 | 2.5 | 1.24 |
| gm soln./gm cat. | 5.0 | 5.0 | 5.0 | 5.0 | 5.0 | 5.0 |
| First Wash: gm/gm cat. | 5.0 | 5.0 | 5.0 | 5.0 | 5.0 | 5.0 |
| Second Treatment: | | | | | | |
| gm salt/1000 gm water | 20.0 | 20.0 | 20.0 | 20.0 | 20.0 | 20.0 |
| gm soln./gm cat. | 2.5 | 2.5 | 2.5 | 2.5 | 2.5 | 2.5 |
| % Soln. Removed by Decanting | 88.3 | 88.2 | 88.0 | 88.4 | 88.0 | 88.3 |
| First Treatment % Chloride Removed, Wt. % (measured by titration) | | | | | | |
| First Treatment | 84.4 | 76.1 | 64.1 | 77.6 | 47.2 | 36.8 |
| Wash | 8.7 | 10.6 | 15.9 | 8.6 | 12.8 | 6.8 |
| Second Treatment | — | 0.8 | 5.4 | 0.5 | 22.5 | 34.5 |
| Total | 93.1 | 87.5 | 85.7 | 86.7 | 82.5 | 78.1 |
| Analysis of Treated Cat., Wt. % | | | | | | |
| Pt, XRF | 0.58 | 0.58 | 0.59 | 0.63 | 0.60 | 0.61 |
| Cl, XRF | 0.10 | 0.11 | 0.12 | 0.11 | 0.14 | 0.17 |
| Na, AA | 1.05 | 0.83 | 0.78 | 0.82 | 0.90 | 0.72 |

TABLE IV

| | | | 600° F. | | | 800° F. | | |
|---|---|---|---|---|---|---|---|---|
| Catalyst | % Cl | % Na | 1,5-DMT Conv. % | Sel. to 1,5-DMN | Wt. % Lights | 1,5-DMT Conv. % | Sel. to 1,5-DMN | Wt. % Lights |
| A1 | 0.10 | 1.05 | 39.0 | 88.5 | 4.22 | 96.4 | 95.4 | 0.58 |
| A2 | 0.11 | 0.83 | 40.8 | 92.3 | 2.99 | 96.2 | 96.3 | −0.01 |
| A3 | 0.12 | 0.78 | 41.7 | 89.5 | 4.04 | — | — | — |
| A4 | 0.11 | 0.82 | 40.4 | 90.4 | 3.29 | 94.7 | 95.1 | 0.81 |
| A5 | 0.14 | 0.90 | 40.9 | 83.6 | 6.21 | 95.2 | 92.9 | 0.81 |
| A6 | 0.17 | 0.72 | 41.8 | 84.4 | 5.99 | 90.2 | 90.2 | 3.35 |

TABLE V

|  | Catalyst | | | | | |
|---|---|---|---|---|---|---|
|  | A7 | A8 | A9 | A10 | A11 | A12 |
| Salt Used | $Na_2CO_3$ | $Na_2CO_3$ | $Na_2CO_3$ | $Na_2CO_3$ | $Na_2CO_3$ | $Na_2CO_3$ |
| First Treatment: | | | | | | |
| gm salt/1000 gm water | 10.0 | 10.0 | 10.0 | 10.0 | 10.0 | 10.0 |
| gm soln./gm cat. | 5.0 | 5.0 | 5.0 | 5.0 | 5.0 | 5.0 |
| First Wash: gm/gm cat. | 5.0 | 10.0 | 5.0 | 5.0 | 5.0 | 5.0 |
| Second Treatment: | | | | | | |
| gm salt/1000 gm water | 0.0 | — | 5.0 | 10.0 | 20.0 | 20.0 |
| gm soln./gm cat. | 2.5 | — | 2.5 | 2.5 | 2.5 | 2.5 |
| % Soln. Removed by Decanting | 87.9 | 87.1 | 87.1 | 88.5 | 88.2 | 87.8 |
| First Treatment % Chloride Removed, Wt. % | | | | | | |

TABLE V-continued

|  | Catalyst | | | | | |
| --- | --- | --- | --- | --- | --- | --- |
|  | A7 | A8 | A9 | A10 | A11 | A12 |
| (measured by titration) | | | | | | |
| First Treatment | 69.1 | 70.5 | 71.8 | 73.4 | 76.1 | 69.5 |
| Wash | 18.9 | 17.2 | 15.5 | 13.7 | 10.2 | 16.2 |
| Second Treatment | 2.7 | — | 1.6 | 1.4 | 0.8 | 1.9 |
| Total | 90.7 | 87.7 | 88.9 | 88.5 | 87.1 | 87.6 |
| Analysis of Treated Cat., Wt. % | | | | | | |
| Pt, XRF | 0.61 | 0.59 | 0.60 | 0.59 | 0.59 | 0.58 |
| Cl, XRF | 0.14 | 0.11 | 0.11 | 0.11 | 0.11 | 0.11 |
| Na, AA | 0.19 | 0.25 | 0.46 | 0.57 | 0.83 | 0.87* |

*Average of two results 0.92 and 0.81.

EXAMPLE VI

Table VI provides data for the dehydrogenation of 1,5-dimethyltetralin to 1,5-dimethylnaphthalene using the catalysts A7 and A9–A12 prepared in Example V. These data demonstrate that a dehydrogenation temperature of 600° F. the selectivity for the catalysts prepared with no or lower concentration of sodium carbonate in the second treatment is lower than for the catalysts prepared using higher concentrations of sodium carbonate for the second treatment. These data indicate that a higher level of residual sodium on the catalyst is generally beneficial for catalyst performance.

TABLE VI

| Catalyst | % Cl | % Na | 600° F. | | | 800° F. | | |
| --- | --- | --- | --- | --- | --- | --- | --- | --- |
|  |  |  | 1,5-DMT Conv. % | Sel. to 1,5-DMN | Wt. % Lights | 1,5-DMT Conv. % | Sel. to 1,5-DMN | Wt. % Lights |
| A7 | 0.14 | 0.19 | 42.2 | 79.2 | 8.47 | 96.0 | 96.9 | −0.13 |
| A8 | 0.11 | 0.25 | — | — | — | — | — | — |
| A9 | 0.11 | 0.46 | 43.3 | 79.2 | 8.31 | 92.5 | 90.5 | 1.49 |
| A10 | 0.11 | 0.57 | 43.3 | 81.8 | 7.04 | 90.2 | 91.0 | 1.60 |
| A11 | 0.11 | 0.83 | 40.9 | 91.6 | 3.19 | 96.2 | 96.0 | 0.17 |
| A12 | 0.11 | 0.87 | 40.2 | 89.4 | 3.81 | 96.3 | 95.1 | 0.33 |

That which is claimed is:

1. A process for dehydrogenating dehydrogenatable organic compounds comprising contacting the organic compound at an elevated temperature with a catalyst formed by the steps comprising:
   (a) contacting a composition comprising a platinum group metal component and a halide component on an alumina support material with an alkaline solution of an alkali metal salt, the amount of solution being in excess of the amount absorbed by the composition;
   (b) partitioning the composition from the remaining solution to form a treated composition and a filtrate containing solubilized halide removed from the composition; and
   (c) drying the treated composition to form the catalyst.

2. The process of claim 1 wherein the dehydrogenatable organic compound is a hydrocarbon containing 2 to about 50 carbon atoms.

3. The process of claim 1 wherein the dehydrogenatable organic compound is a linear alkane containing about 2 to about 30 carbon atoms.

4. The process of claim 1 wherein the dehydrogenatable organic compound is a dimethyltetralin or a dimethyldecalin.

5. The process of claim 1 wherein the dehydrogenatable organic compound is 1,5-dimethyltetralin, 1,6-dimethyltetralin, 2,5-dimethyltetralin or 2,6-dimethyltetralin.

6. The process of claim 1 wherein the platinum group metal component comprises platinum.

7. The process of claim 1 wherein the alkali metal salt is a bicarbonate, carbonate, hydroxide or oxide.

8. The process of claim 1 wherein the salt is sodium carbonate.

9. The process of claim 1 wherein the amount of solution is at least about 1 part by weight per part by weight of the composition.

10. The process of claim 7 wherein the alkaline solution contacted with the composition comprises about 1 to about 100 parts by weight of the alkali metal salt.

11. The process of claim 1 wherein the filtrate has a pH above about 7.

12. The process of claim 1 wherein the halide comprises chloride and wherein the catalyst contains no more than about 0.14 weight percent chloride.

13. The process of claim 1 wherein after step (b), the treated composition is contacted with water to remove at least a major portion of the alkaline solution absorbed by the composition to form a water washed composition; the water washed composition is contacted with a solution of an alkali metal salt to form a second treated composition, and the second treated composition is dried to form the catalyst.

14. A method for dehydrogenating a dimethyltetralin to a dimethylnaphthalene comprising contacting the dimethyltetralin at an elevated temperature with a dehydrogenation catalyst comprising alumina, about 0.05 to about 5 weight percent platinum or palladium, no more than about 0.14 weight percent halide, and about 0.10 to about 2.0 weight percent alkali metal, all weight percents being based on the total weight of the catalyst.

* * * * *